US00PP08593P

United States Patent [19]

Warriner, deceased

[11] Patent Number: Plant 8,593

[45] Date of Patent: Feb. 15, 1994

[54] HYBRID TEA ROSE PLANT NAMED 'JACMAD'

[75] Inventor: William A. Warriner, deceased, late of Tustin, Calif., by Alene Beatrice Warriner, legal representative

[73] Assignee: Bear Creek Gardens, Inc., Medford, Oreg.

[21] Appl. No.: 953,531

[22] Filed: Sep. 28, 1992

[51] Int. Cl.[5] ..... A01H 5/00

[52] U.S. Cl. ..... Plt./12

[58] Field of Search ..... Plt. 11, 12

*Primary Examiner*—Howard J. Locker

*Attorney, Agent, or Firm*—Klarquist, Sparkman, Campbell, Leih and Whinston

[57] ABSTRACT

Hybrid tea rose plant having strong, vigorous, upright growth habit; distinctive red and yellow bicolor flowers; dark green, glossy foliage, and free-flowering ability.

1 Drawing Sheet

The present invention relates to a new and distinct variety of rose plant of the Hybrid tea class which was originated by the inventor by crossing the variety JAColite, U.S. Plant Pat. No. 4,167, with the variety Madras, U.S. Plant Pat. No. 4,460.

The primary objective of this breeding was to produce a new rose variety having the upright vigorous growth and excellent flower form of JAColite combined with the free-flowering ability of Madras and its rose pink color. The objective was substantially achieved along with other desirable improvements as evidenced by the following unique combination of characteristics which are outstanding in the new variety and which distinguish it from its parents, as well as from all other varieties of which I am aware:

1. Vigorous upright growth habit;
2. Distinct bicolor flower;
3. Dark green glossy foliage;
4. Very free flowering.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—JAColite, U.S. Plant Pat. No. 4,167.

*Pollen parent.*—Madras, U.S. Plant Pat. No. 4,460.

Classification:

*Botanical.*—Rosa hybrida.

*Commercial.*—Hybrid tea.

FLOWER

Observations made from specimens grown in a garden environment in Somis, Calif., from April through June, 1992.

Blooming habit: Recurrent.

Bud:

*Size.*—1½ inches when the petals start to unfurl.

*Form.*—*Pointed ovoid.*

*Color.*—When sepals first divide, bud color is Red Group 50A at the petal tips with a strong undertone of Yellow Group 11A toward the petal base. When half blown, the upper sides of the petals are Red Group 50A; and the lower sides of the petals are Yellow Group 11D with the yellow stronger, Yellow Group 11A, toward the petal base.

*Sepals.*—Color: Green Group 138C. Surface texture: Covered with fine hairs. There are three normally appendaged sepals. There are two unappendaged sepals with hairy edges.

*Receptacle.*—Color: Green Group 137C. Shape: Apple. Size: Large, ⅜×¼ inch. Surface: Smooth.

*Peduncle.*—Length: Short, 2½ inches. Surface: Smooth with occasional glands. Color: Medium green. Strength: Stiff, erect.

Bloom:

*Size.*—Large. Average open size is 4½ .

*Borne.*—Singly.

*Stems.*—Medium, 14 to 18 inches.

*Form.*—When first open: High centered. Permanence: Retains its form to the end, outer petals curl back.

*Petalage.*—Number of petals under normal conditions: 25-30.

*Color.*—The upper side of the petals is Red Group 50A. The reverse side of the petals is Yellow Group 11C. The major color on the upper side is Red Group 50A.

*Variegations.*—None.

*Discoloration.*—The general tonality at the end of the first day: No change. At the end of the third day: No change.

*Fragrance.*—Slight.

Petals:

*Texture.*—Thick.

*Shape.*—Round.

*Form.*—Tips slightly recurved.

*Arrangement.*—Imbricated, with few petaloids in the center.

*Persistence.*—Drop off cleanly.

*Lastingness.*—On the plant: Long, 5–6 days. As a cut flower: Long, 7–8 days.

Reproductive parts:

*Anthers.*—Size: medium. Quantity: Many. Color: Yellow. Arrangement: Regular around styles.

*Filaments.*—Color: Reddish brown.

*Pollen.*—Color: Gold yellow.

*Styles.*—Color: Reddish.

*Stigmas.*—Color: Greenish white.

Form: Bush.

Growth: Very vigorous, upright and branching.

Foliage:

*Number of leaflets on normal mid-stem leaves.*—5 or 7.

*Size.*'Large, 5×4 inches.

*Quantity.*—Abundant.

*Color.*—New foliage: Reddish. Old Foliage: Dark glossy green.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth, with occasional prickles.

*Stipules.*—Medium, bearded and glandular.

*Disease resistance.*—Susceptible to mildew but resistant to rust under normal growing conditions at Somis, Calif.

Wood:

*New wood.*—Color: Reddish. Bark: Smooth.

Old wood.—Color: Green. Bark: Smooth.

Prickles:

*Quantity.*—On main canes from base: Ordinary. On laterals from main canes: Ordinary.

*Form.*—Medium, hooked downward.

*Color when young.*—Red.

Small prickles:

*Quantity.*—On main stalks: None. On Laterals: None.

I claim:

1. A new and distinct variety of rose plant of the hybrid tea class, substantially as herein shown and described, characterized particularly as to novelty by the unique combination of its strong, vigorous, upright, grown habit; its distinctive bicolor flowers; its dark green, glossy foliage, and its free-flowering ability.

* * * * *

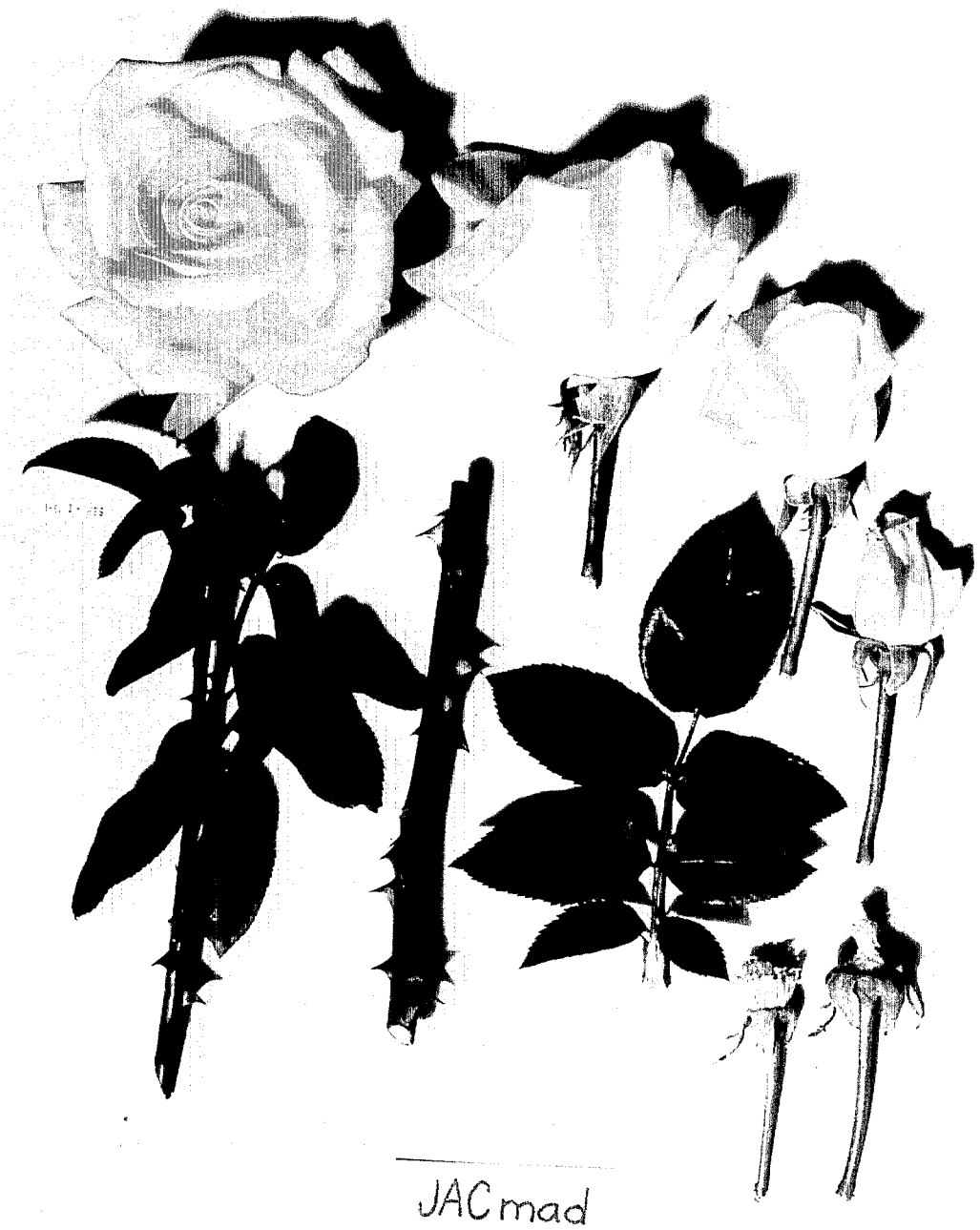
JACmad

UNITED STATES PATENT AND TRADEMARK OFFICE

CERTIFICATE OF CORRECTION

PATENT NO. : PP 8,593

DATED : February 15, 1994

INVENTOR(S) : William A. Warriner, deceased

It is certified that error appears in the above-identified patent and that said Letters Patent is hereby corrected as shown below:

Column 4, line 24, "grown" should be --growth--.

Signed and Sealed this

Eighteenth Day of October, 1994

Bruce Lehman

*Attest:*

BRUCE LEHMAN

*Attesting Officer*

*Commissioner of Patents and Trademarks*